(12) United States Patent
Franchini et al.

(10) Patent No.: US 8,804,457 B2
(45) Date of Patent: Aug. 12, 2014

(54) TRANSMIT/RECEIVE SYSTEMS FOR IMAGING DEVICES

(75) Inventors: Luigi Franchini, Rimini (IT); Roberto Alini, Dublin City, CA (US); Filippo Cevini, Campbell City, CA (US)

(73) Assignee: Maxim Integrated Products, Inc., San Jose, CA (US)

( * ) Notice: Subject to any disclaimer, the term of this patent is extended or adjusted under 35 U.S.C. 154(b) by 483 days.

(21) Appl. No.: 13/077,252

(22) Filed: Mar. 31, 2011

(65) Prior Publication Data

US 2012/0250462 A1 Oct. 4, 2012

(51) Int. Cl.
*G01S 7/52* (2006.01)

(52) U.S. Cl.
CPC .................................. *G01S 7/52004* (2013.01)
USPC .......................................................... 367/87

(58) Field of Classification Search
USPC .......................................................... 367/87
See application file for complete search history.

(56) References Cited

U.S. PATENT DOCUMENTS

| | | | | |
|---|---|---|---|---|
| 3,964,297 | A * | 6/1976 | Jorgensen et al. | 73/609 |
| 4,538,469 | A * | 9/1985 | Lynnworth et al. | 73/861.27 |
| 4,926,380 | A * | 5/1990 | Harada | 367/7 |
| 6,074,346 | A * | 6/2000 | Oppelt | 600/437 |
| 6,192,760 | B1 * | 2/2001 | MacLauchlan et al. | 73/643 |
| 2006/0061231 | A1 | 3/2006 | Kameishi | 310/314 |
| 2009/0102443 | A1 * | 4/2009 | Smith | 323/282 |
| 2009/0240144 | A1 * | 9/2009 | Teo | 600/437 |
| 2010/0254221 | A1 * | 10/2010 | Smith | 367/137 |

FOREIGN PATENT DOCUMENTS

CN 1751662 A 3/2006

OTHER PUBLICATIONS

Office Action dated Dec. 17, 2013 from the Chinese Patent Office for Chinese Patent Application No. 201210093609.9.
English Translation of Office Action dated Dec. 17, 2013 from the Chinese Patent Office for Chinese Patent Application No. 201210093609.9.
Wodnicki, Robert et al., "Electronics for Diagnostic Ultrasound", Medical Imaging: Principles, Detectors, and Electronics, edited by Krzysztof Iniewski, 2009 John Wiley & Sons, Inc., pp. 167-220.

* cited by examiner

*Primary Examiner* — Isam Alsomiri
*Assistant Examiner* — James Hulka

(57) ABSTRACT

A transceiver for an ultrasonic imaging device includes a transmit circuit and a receive circuit. The transmit circuit outputs test pulses to a probe including a transducer to generate an image of a test object. A composite signal including the test pulses and a reflected signal is output by the transducer. The receive circuit receives the composite signal including the test pulses and the reflected signal and includes a filter circuit. The filter circuit filters the test pulses from the composite signal and passes the reflected signal. An impedance of the filter circuit is equal to substantially zero when the reflected signal is within a predetermined frequency range.

18 Claims, 6 Drawing Sheets

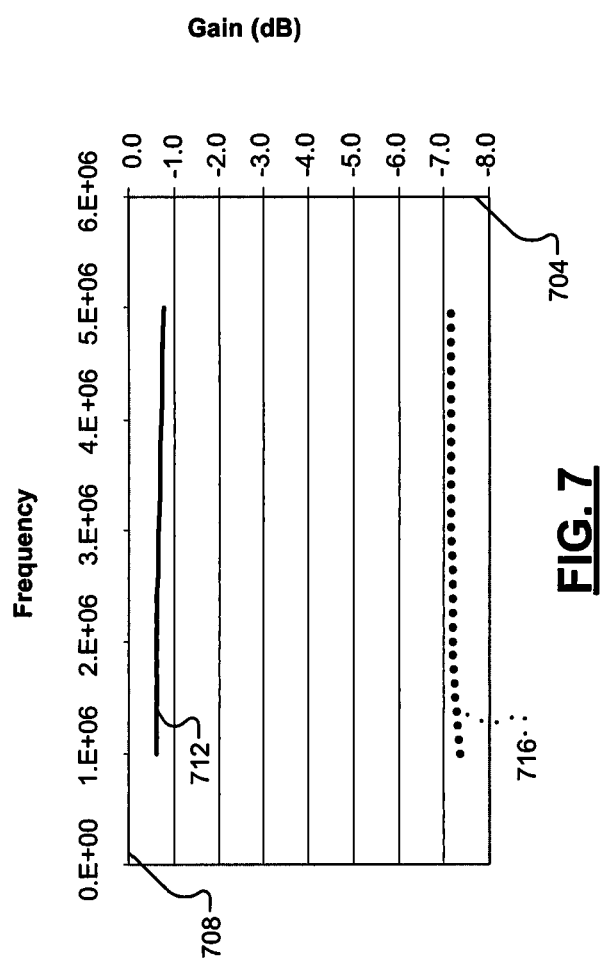

TRANSMIT/RECEIVE SYSTEMS FOR IMAGING DEVICES

FIELD

The present disclosure relates to imaging devices and more particularly to Transmit/Receive (T/R) circuits for imaging devices.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

External features of an object can be viewed by a human eye and captured via conventional imaging devices, such as a camera. Internal features of the object, however, generally cannot be readily observed. Ultrasonic imaging devices are used in various fields. For example only, an ultrasonic imaging device may be used for medical imaging, non-destructive testing, non- and minimally-invasive testing, and other fields.

An ultrasonic imaging device generally includes one or more transmitters and one or more receivers. The transmitters generate test signals that are applied to a probe. The probe includes transducers that move based on the test signals. When the probe is in contact with an object, movement of the transducers causes a wave to propagate through the object. Reflected waves also cause the transducers to move, and the transducers output reflected signals. An image of the internal features of the object can be generated based on the reflected signals.

SUMMARY

A transceiver for an ultrasonic imaging device includes a transmit circuit and a receive circuit. The transmit circuit outputs test pulses to a probe including a transducer to generate an image of a test object. A composite signal including the test pulses and a reflected signal is output by the transducer. The receive circuit receives the composite signal including the test pulses and the reflected signal and includes a filter circuit. The filter circuit filters the test pulses from the composite signal and passes the reflected signal. An impedance of the filter circuit is equal to substantially zero when the reflected signal is within a predetermined frequency range.

In further features, a transceiver for an ultrasonic imaging device includes a transmit circuit and a diode bridge. The transmit circuit outputs test pulses to a probe including a transducer to generate an image of a test object. A composite signal including the test pulses and a reflected signal is output by the transducer. The diode bridge receives the composite signal including the test pulses and the reflected signal. The diode bridge filters the test pulses from the composite signal and passes the reflected signal. Each of the diodes of the diode bridge has a forward transit time that is greater than one divided by a product of $2\pi$ and a minimum value of a predetermined frequency range of the reflected signal.

In still further features, a transceiver for an ultrasonic imaging device includes a transmit circuit, a diode bridge, and a bias resistor. The transmit circuit outputs test pulses of a first magnitude to a probe including a transducer to generate an image of a test object. A composite signal including the test pulses and a reflected signal is output by the transducer. A maximum magnitude of the reflected signal is less than the first magnitude. The diode bridge receives the composite signal including the test pulses and the reflected signal and includes diodes having forward transit times that are each greater than one divided by a product of $2\pi$ and a minimum value of a predetermined frequency range of the reflected signal. The bias resistor is connected between a bias voltage and the diode bridge. A second magnitude of the bias voltage is greater than the maximum magnitude and less than the first magnitude. The diode bridge filters voltages of the composite signal that are greater than the bias voltage and passes voltages of the composite signal that are less than the bias voltage.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIGS. 6-7 are example graphs of gain as a function of frequency.

DETAILED DESCRIPTION

Figure 1:
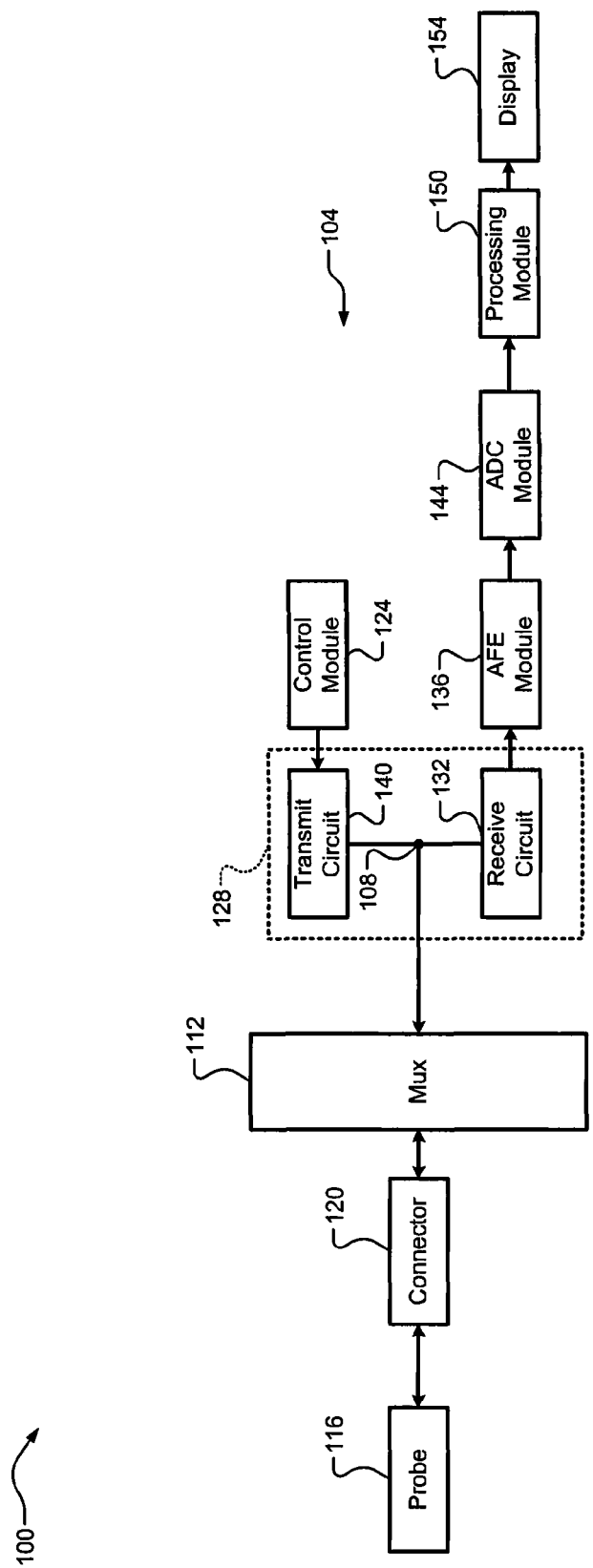
FIG. 1 is a functional block diagram of an example imaging system according to the present disclosure.

The following description is merely illustrative in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

An imaging device, such as an ultrasonic imaging device, includes a transmit circuit and a receive circuit. The transmit circuit selectively generates test pulses. A transducer of a probe moves based on the test pulses to propagate an ultrasonic wave through an object.

The transducer also senses reflected waves. The transducer outputs a reflected signal based on reflected waves. The receive circuit receives signals based on the test pulses and the reflected waves. The receive circuit filters the test pulses and passes the reflected signal.

The receive circuit may include a diode bridge. The diodes of the diode bridge have forward transit times that are greater than a predetermined value. The predetermined value may be greater than $1/(2*\pi*f)$, where f is a predetermined minimum frequency of the reflected signal. The predetermined minimum frequency is greater than zero and less than a predetermined maximum frequency of the reflected signal.

Using diodes with forward transit times that are greater than the predetermined value ensures that a cutoff frequency of the diode bridge is less than the predetermined minimum frequency. When the cutoff frequency of the diode bridge is less than the predetermined minimum frequency, the diode bridge has an impedance of substantially zero between the predetermined minimum frequency and the predetermined maximum frequency. The diode bridge having an impedance of substantially zero may mean that the impedance of the diode bridge is approximately equal to an equivalent parasitic series resistor. When the forward transit times are greater than the predetermined value, a decrease in power dissipation and/or one or more other benefits may be realized relative to a diode bridge with diodes having forward transit times that are less than the predetermined value.

Referring now to FIG. 1, a functional block diagram of an example implementation of an imaging system 100 is presented. The imaging system 100 may be, for example, of a medical imaging device, a non-destructive testing device, or another suitable type of device. The imaging system 100 may be implemented in a portable or a non-portable device. Portable devices may be powered via one or more batteries, while non-portable devices may be powered via a utility.

The imaging system 100 includes a transmit/receive (T/R) path 104. While only the T/R path 104 is shown, a given imaging device may include a plurality of T/R paths. A T/R path can also be referred to as a T/R channel. The T/R path 104 includes a T/R node 108 that is connected to a multiplexer 112. An imaging probe 116 includes one or more transducers, such as transducer 118, that may be connected to the multiplexer 112 via one or more electrical connectors 120. In various implementations, the multiplexer 112 may be omitted. For example only, the transducer 118 may include a piezoelectric transducer. In various implementations, more than one probe may be associated with a given T/R path.

The T/R path 104 includes a control module 124, a T/R circuit 128, an AFE module 136, and an ADC module 144. In various implementations, the T/R circuit 128 and the AFE module 136 may be implemented independently or within a single chip. The control module 124 outputs a control signal to the T/R circuit 128 for propagating an ultrasonic wave through an object.

The T/R circuit 128 includes both a transmit circuit 140 and a receive circuit 132. The transmit circuit 140 generates a test signal based on the control signal and outputs the test signal to the T/R node 108. When the transmit circuit 140 is outputting the test signal to the T/R node 108, a switch of the multiplexer 112 may be actuated to connect the T/R node 108 with the transducer 118. In various implementations, the T/R node 108 may be directly connected to the transducer 118. The transducer 118 moves based on the test signal and causes a pressure wave to propagate into the object.

Reflected pressure waves also cause the transducer 118 to move. The transducer 118 senses reflected waves and outputs a reflected (electrical) signal based on the reflected waves. The T/R node 108 receives both the test signal and the reflected signal. The receive circuit 132 filters/blocks the test signal. The receive circuit 132 may minimize attenuation of the reflected signal before providing it to the AFE module 136. In various implementations, the receive circuit 132 may also perform amplification.

The AFE module 136 may perform one or more analog functions, such as amplifying, and filtering, before outputting an imaging signal to the ADC module 144. The ADC module 144 may selectively generate digital samples based on the imaging signal and output the digital samples to a processing module 150. The processing module 150 may process the digital samples output by the ADC module 144 and other ADC modules to generate an image of internal features of the object. The image may be displayed via a display 154.

Figure 2:
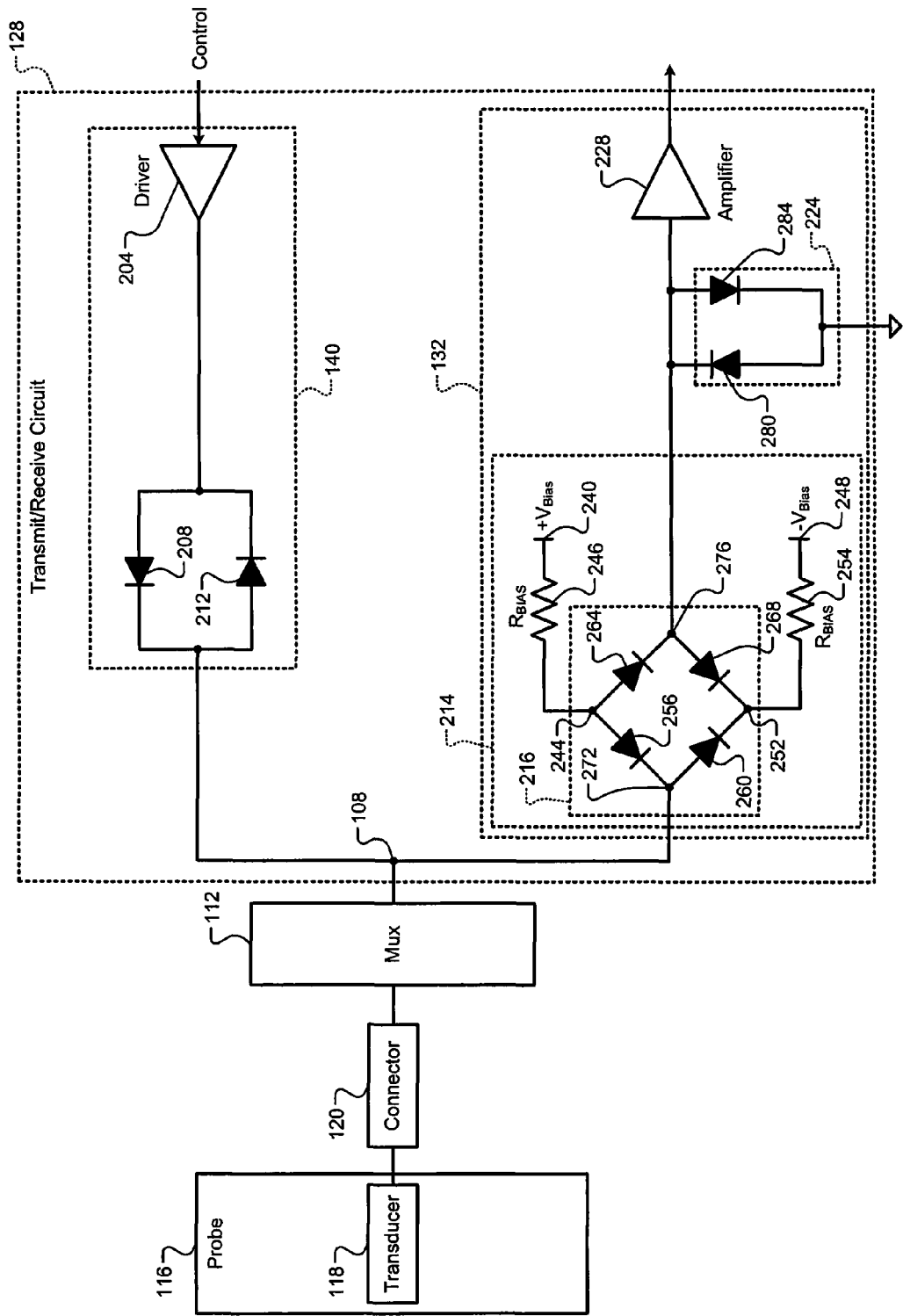
FIG. 2 is a schematic of an example transmit/receive path of the imaging system according to the present disclosure.

Referring now to FIG. 2, a functional block diagram of example implementations of the transmit circuit 140 and the receive circuit 132 is presented. A driver 204 may generate the test signal based on the control signal. More specifically, the driver 204 selectively generates voltage pulses in the test signal. For example only, the voltage pulses may be unipolar pulses between a first predetermined voltage and a reference potential (e.g., ground), bipolar pulses between positive and negative values of a first predetermined voltage, multi-level pulses, or another suitable type of pulses. For example only, the first predetermined voltage may be between 5 Volts (V) and 300 V, inclusive, and may be approximately 100 V in various implementations. By way of contrast, the magnitude of the reflected signal may be in the range of tens of microvolts (μV) to hundreds of millivolts (mV) or other voltages that are less than the first predetermined voltage.

The operating frequency of the test signal may be between a predetermined minimum frequency and a predetermined maximum frequency. For example only, the predetermined minimum and maximum frequencies may be approximately 1 megahertz (MHz) and 10 megahertz (MHz), respectively, or other suitable values. The operating frequency of the test signal may be set based on a user input or another suitable input. The transmit circuit 140 may output the test signal to the T/R node 108 via a pair of anti-parallel diodes 208 and 212.

A predetermined frequency range (of interest) of the reflected signal may be between a predetermined minimum frequency and a predetermined maximum frequency. For example only, the predetermined minimum and maximum frequencies may be approximately 1 megahertz (MHz) and 10 megahertz (MHz), respectively, or other suitable values.

The receive circuit 132 may include a filter circuit 214 that may include a diode bridge 216, a clipper circuit 224, and an amplifier 228. A first bias resistor 246 may be connected between a positive bias voltage 240 and a first node 244 of the diode bridge 216. A second bias resistor 254 may be connected between a negative bias voltage 248 and a second node 252 of the diode bridge 216. The positive and negative bias voltages 240 and 248 may be, for example, +/−5 V, +/−12 V, or another suitable voltage that is less than the first predetermined voltage and greater than a maximum value of the reflected signal. The application of the bias voltage to the diode bridge 216 causes a bias current to flow.

The diode bridge 216 may include four diodes: a first diode 256, a second diode 260, a third diode 264, and a fourth diode 268. While the diode bridge 216 is shown and described as including a full-bridge, the diode bridge 216 may include a half-bridge in various implementations. The anodes of the first and third diodes 256 and 264 are connected to the first node 244. The cathode of the first diode 256 is connected to an input node 272 of the diode bridge 216, and the input node 272 is connected to the T/R node 108. The cathode of the third diode 264 is connected to an output node 276 of the diode bridge 216, and the output node 276 is connected to the clipper circuit 224 and the amplifier 228. The anodes of the second and fourth diodes 260 and 268 are connected to the input and output nodes 272 and 276, respectively. The cathodes of the second and fourth diodes 260 and 268 are connected to the second node 252.

The filter circuit 214 blocks the test signal. The filter circuit 214 allows the reflected signal to pass from the input node 272 to the output node 276. For example only, because the magnitude of the test signal is greater than the magnitude of the bias voltage, the diodes of the diode bridge 216 are reverse biased when the test signal is present at the T/R node 108. Accordingly, the diodes of the diode bridge 216 prevent current output by the transmit circuit 140 from flowing between the input node 272 and the output node 276. Because the magnitude of the reflected signal is less than the magnitude of the bias voltage, however, the diodes of the diode bridge 216 are forward biased and allow current to flow between the input node 272 and the output node 276.

The clipper circuit 224 may include fifth and sixth diodes 280 and 284. The cathode of the fifth diode 280 and the anode of the sixth diode 284 may be connected to the output node 276. The anode of the fifth diode 280 and the cathode of the sixth diode 284 may be connected to a reference potential, such as ground. The amplifier 228 is also connected to the output node 276.

The clipper circuit 224 limits the magnitude of the voltage input to the amplifier 228 (i.e., the voltage at the output node 276) to less than the magnitude of the bias voltage. The amplifier 228 may include, for example, a low noise amplifier (LNA) or another suitable type of amplifier. In various implementations, the clipper circuit 224 and/or the amplifier 228 may be implemented independently or within the AFE module 136.

Figure 4:
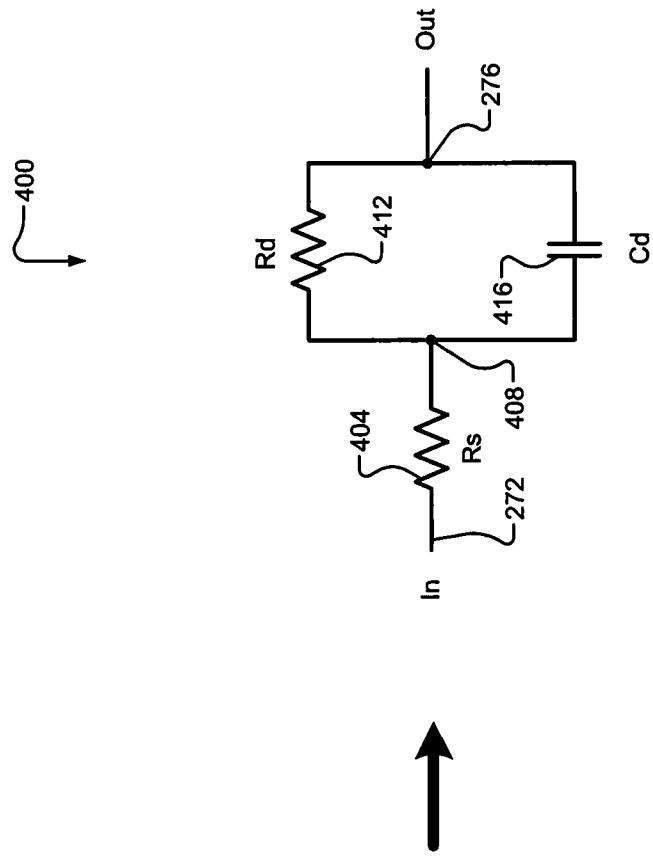
FIG. 4 is a schematic of a small-signal equivalent circuit of the receive circuit of FIG. 3.
Figure 3:
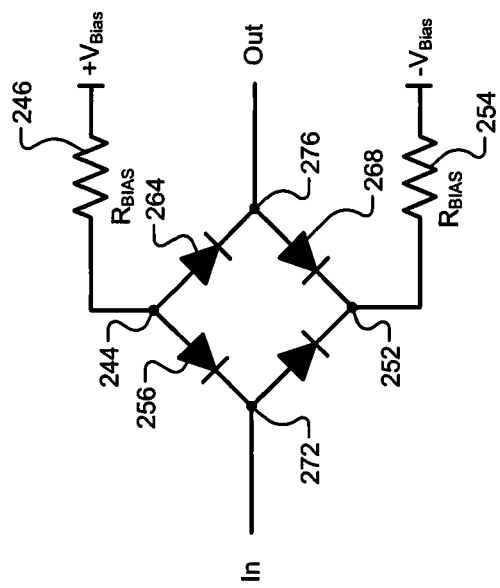
FIG. 3 is a partial schematic of a receive circuit according to the present disclosure.

FIG. 3 is an example schematic of the filter circuit 214 of the receive circuit 132. FIG. 4 is a small-signal equivalent circuit 400 of the filter circuit 214 of FIG. 3, assuming that the first and second bias resistors 246 and 254 are greater than the ON resistance ($R_{ON}$) of the diode bridge 216. Because the diode bridge 216 includes two parallel signal paths, each path having two diodes in series, the input to output impedance of the diode bridge 216 can be approximated in the first-order as a single equivalent diode for small-signal equivalent circuit purposes.

Referring now to FIG. 4, the small-signal equivalent circuit 400 includes an equivalent (parasitic) series resistor ($R_s$) 404 connected between the input node 272 and a third node 408. The small-signal equivalent circuit 400 also includes an equivalent diode resistor ($R_d$) 412 and a diffusion capacitor ($C_d$) 416 that are both connected between the third node 408 and the output node 276. The resistance of the equivalent diode resistor 412 is generally greater than the resistance of the equivalent series resistor 404.

The resistance of the equivalent diode resistor 412 can be determined based on:

$$R_d = \frac{1}{g_m},$$

where $R_d$ is the resistance of the equivalent diode resistor 412 and $g_m$ is the transconductance of the single equivalent diode. The transconductance of the single equivalent diode ($g_m$) can be determined based on:

$$g_m = \frac{I_d}{V_t},$$

where $g_m$ is the transconductance of the single equivalent diode, $I_d$ is the forward bias current through each diode of the diode bridge 216 and is or is approximately one half of the current flowing from the positive bias voltage 240 to the negative bias voltage 248, and $V_t$ is the thermal voltage of the single equivalent diode. The capacitance of the diffusion capacitor 416 can be determined based on:

$$C_d = T_{fw} * g_m,$$

where $C_d$ is the capacitance of the diffusion capacitor 416, $T_{fw}$ is the forward transit time (seconds) of the single equivalent diode, and $g_m$ is the transconductance of the single equivalent diode.

Figure 5:
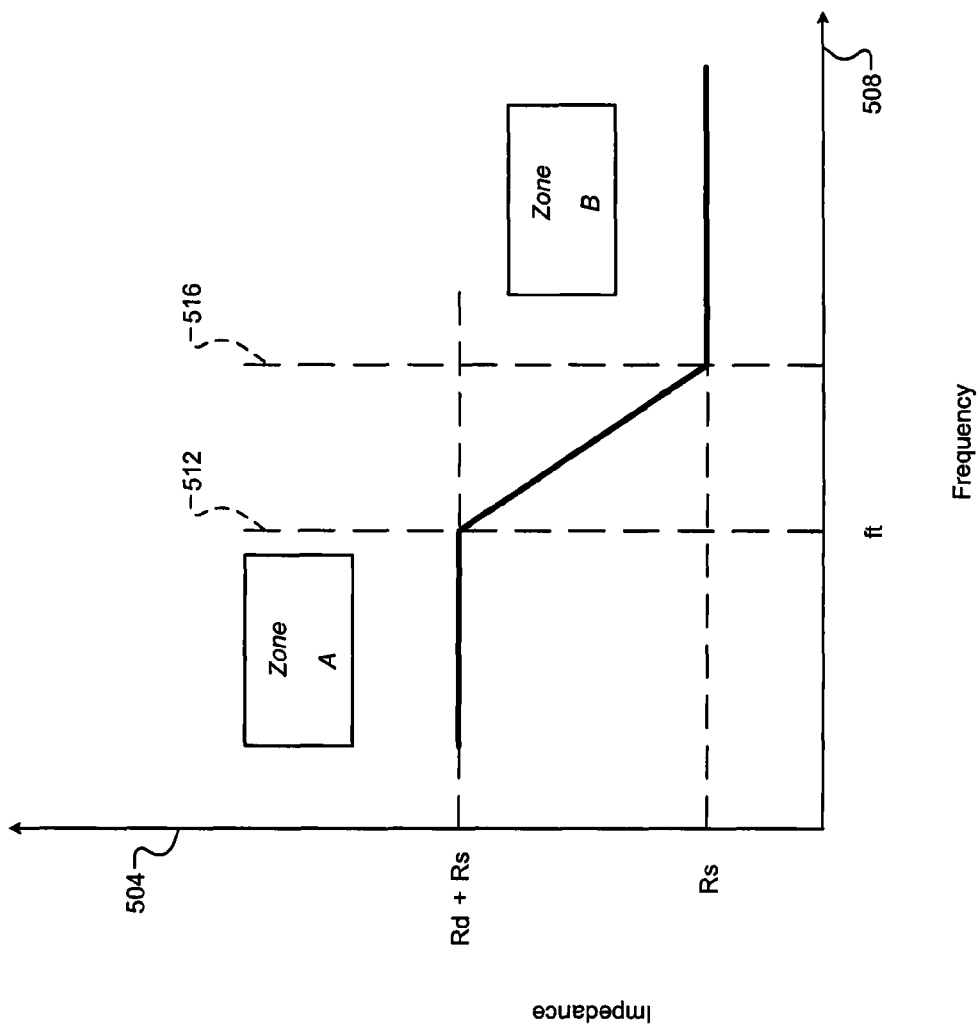
FIG. 5 is an example graph of impedance as a function of frequency.

FIG. 5 is a graph of impedance 504 of the small-signal equivalent circuit 400 as a function of frequency 508. When the frequency of the reflected signal is less than a cutoff frequency ($f_t$) 512, the impedance of the small-signal equivalent circuit 400 may be approximately equal to the sum of resistance of the equivalent diode resistor 412 and the resistance of the equivalent series resistor 404 (i.e., $R_d + R_s$). The impedance of the small-signal equivalent circuit 400 being approximately equal to the sum of the resistance of the equivalent diode resistor 412 and the resistance of the equivalent series resistor 404 may be attributable to the diffusion capacitor 416 acting substantially as an open-circuit at frequencies less than the cutoff frequency 512. When acting substantially as an open-circuit may mean that at least a predetermined percent of the current flowing between the third node 408 and the output node 276 will be forced to flow through the equivalent diode resistor 412. For example only, the predetermined percent may be greater than approximately 95 percent, 96 percent, 97 percent, 98 percent, 99 percent, or another suitable value. When the frequency of the reflected signal is less than the cutoff frequency 512, the filter circuit 214 will be referred to as operating in Zone A.

The impedance of the small-signal equivalent circuit 400 may decrease as the frequency increases between the cutoff frequency 512 and a second frequency 516. The decrease in the impedance may be attributable to the diffusion capacitor 416 increasingly acting as a short circuit as the frequency of the reflected signal increases. At frequencies greater than the second frequency 516, the impedance of the small-signal equivalent circuit 400 may be approximately equal to the resistance of the equivalent (parasitic) series resistor 404 (i.e., $R_s$) only. The filter circuit 214 will be referred to as operating in Zone B when operating at frequencies that are greater than the second frequency 516.

The impedance of the small-signal equivalent circuit 400 being approximately equal to the resistance of the equivalent series resistor 404 only may be attributable to the diffusion capacitor 416 effectively shunting the equivalent diode resistor 412 during operation in Zone B. More specifically, during operation in Zone B, the diffusion capacitor 416 may act substantially as a short circuit. Noise generated by the equivalent diode resistor 412 may therefore be shunted by the diffusion capacitor 416 and reduce or be a non-contributor to the noise present at the output node 276 during operation in Zone B.

Acting substantially as a short circuit may mean that the diffusion capacitor 416 allows at least a first predetermined percent of the current flowing between the third node 408 and the output node 276 to bypass the equivalent diode resistor 412. In this manner, the impedance associated with the equivalent diode resistor 412 and the diffusion capacitor 416 may be substantially zero at frequencies greater than the second frequency 516. The impedance associated with the equivalent diode resistor 412 and the diffusion capacitor 416 being substantially zero may mean less than a second predetermined percent of the impedance associated with the equivalent diode resistor 412 and the diffusion capacitor 416 impedance at and below the cutoff frequency 512 ($R_s + R_d$). For example only, this predetermined percentage may be approximately 5 percent, approximately 4 percent, approximately 3 percent, approximately 2 percent, approximately 1 percent, or another suitable value. When the impedance associated with the equivalent diode resistor 412 and the diffusion capacitor 416 is substantially zero, the impedance of the small-signal equivalent circuit 400 may be said to be equal to substantially zero. The impedance of the small-signal equivalent circuit 400 being substantially zero may mean equal to a sum of the resistance of the equivalent (parasitic) series resistor 404 and the substantially zero impedance associated with the equivalent diode resistor 412 and the diffusion capacitor 416.

Cutoff frequency ($f_t$) is related to forward transit time ($T_{fw}$). For example only, the cutoff frequency can be determined based on:

$$f_t = \frac{1}{2 * \pi * T_{fw}} = \frac{1}{2 * \pi * R_d * C_d},$$

where $f_t$ is the cutoff frequency, $\pi$ is the mathematical constant Pi, $R_d$ is the resistance of the equivalent diode resistor 412, and $R_s$ is the resistance of the equivalent series resistor 404.

The forward transit times of diodes of a given diode bridge may be approximately 4-6 nanoseconds (ns) in various implementations. However, the given diode bridge would operate in Zone A when the reflected signal is received from the probe 116. If the given diode bridge operates in Zone A, the input/output ON resistance of the given diode bridge and the noise generated by the given diode bridge is inversely related to the bias current.

Accordingly, the bias current would have to be increased in order to decrease the ON resistance of the given diode bridge and the noise generated by the given diode bridge. Increasing the bias current, however, increases the amount of power that is dissipated by the given diode bridge and lost. A decrease in power dissipation may be especially beneficial to portable (e.g., handheld) imaging devices that rely on one or more batteries for power.

An increase in the bias current can be accomplished by decreasing the resistances of the first and second bias resistors used with the given diode bridge. However, based on the decrease in the load seen by the transmit circuit 140 and to reduce the noise generated by the bias resistors, external inductors in series with the bias resistors, respectively, may need to be included. The addition of the external inductors, however, may increase package size and price and may require that each T/R circuit be supplied with additional input/output (I/O) pins for external connection to the external inductors.

The first, second, third, and fourth diodes 256, 260, 264, and 268 of the present disclosure have forward transit times that are greater than a predetermined period. More specifically, the forward transit times of the first, second, third, and fourth diodes 256, 260, 264, and 268 are such that the cutoff frequency 512 and the second frequency 516 are less than the predetermined minimum frequency of the reflected signal. For example only, the forward transit times of the first, second, third, and fourth diodes 256, 260, 264, and 268 can be expressed by:

$$T_{fw} > \frac{1}{2 * \pi * f_{Min}},$$

where $T_{fw}$ is the forward transit time of the first, second, third, and fourth diodes 256, 260, 264, and 268, $\pi$ is the mathematical constant Pi, and $f_{Min}$ is the predetermined minimum frequency of the reflected signal. The predetermined minimum frequency is greater than zero, and the predetermined maximum frequency is greater than the predetermined minimum frequency. For example only, if the predetermined minimum frequency is 1 Megahertz (MHz), the forward transit times may be greater than approximately 250 nanoseconds (ns).

When the cutoff frequency and the second frequency are less than the predetermined minimum frequency, the diode bridge 216 may operate in Zone B at operating frequencies between the predetermined minimum frequency and the predetermined maximum frequency, inclusive. If the diode bridge 216 operates in Zone B, the ON resistance of (and therefore the insertion loss attributable to) the diode bridge 216 is independent of the bias current.

The diode bridge 216 can therefore operate with a lower bias current relative to a diode bridge with diodes having forward transit times that are less than the predetermined period. For example only, the diode bridge 216 can operate with a bias current of approximately 1.5 milliamps (mA) or less while a diode bridge with diodes having forward transit times that are less than the predetermined period may operate with a bias current of approximately 10 mA or more to provide a similar total input/output ON resistance and a similar amount of noise. The lower bias current may enable the diode bridge 216 to provide a decrease in the amount of power dissipated relative to the power dissipation of a diode bridge with diodes having forward transit times that are less than the predetermined period. For example only, the power dissipation may be reduced by approximately a factor of 10 or more. Additionally, the diode bridge 216 can operate without external inductors, and the diode bridge 216 may provide a higher power supply rejection ratio (PSRR) than a diode bridge with diodes having forward transit times that are less than the predetermined period.

Figure 6:
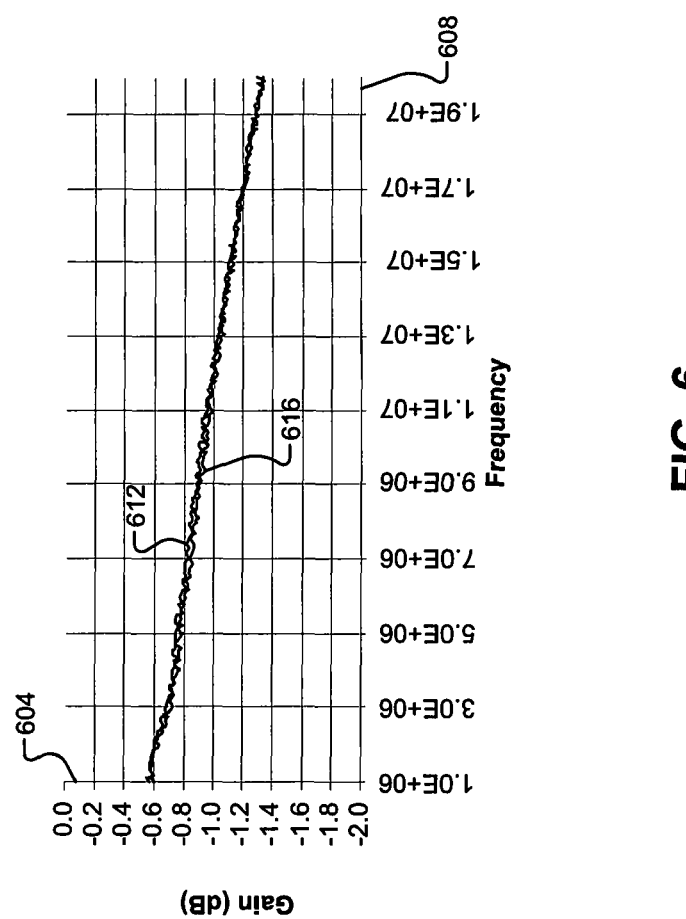

Referring now to FIG. 6, an example graph of gain 604 of the diode bridge 216 as a function of frequency 608 is presented. The diodes of the diode bridge 216 have forward transit times that are greater than the predetermined value such that the cutoff frequency and the second frequency are less than the predetermined minimum frequency. Example trace 612 tracks the gain 604 of the diode bridge 216 as a function of the frequency 608 with a bias current of approximately 1.5 milliamps (mA). Example trace 616 tracks the gain 604 of the diode bridge 216 as a function of the frequency 608 with a bias current of approximately 3.0 mA. The similarity of the example traces 612 and 616 may indicate that the ON resistance (and therefore the insertion loss) of the diode bridge 216 is independent of the bias current when the diodes have forward transit times that are greater than the predetermined value.

Referring now to FIG. 7, an example graph of gain 704 as a function of frequency 708 for various diode bridges is presented. Example solid trace 712 tracks the gain 704 of a second diode bridge as a function of the frequency 708. The diodes of the second diode bridge have forward transit times that are less than the predetermined value. Example dashed trace 716 tracks the gain 704 of the diode bridge 216 as a function of the frequency 708. The diodes of the diode bridge 216 have forward transit times that are greater than the predetermined value. The example traces 712 and 716 are graphed with the diode bridge 216 and the second diode bridge being biased with a 1.5 mA bias current and driving a 50 Ohm load. The difference in the gain 704 between the example traces 712 and 716 indicates that the diodes of the diode bridge 216 with forward transit times that are greater than the predetermined value may provide an improvement in the gain 704 of approximately 6.5 decibels (dB).

The broad teachings of the disclosure Can be implemented in a variety of forms. Therefore, while this disclosure includes particular examples, the true scope of the disclosure should not be so limited since other modifications will become apparent to the skilled practitioner upon a study of the drawings, the specification, and the following claims.

What is claimed is:

1. A transceiver for an ultrasonic imaging device, comprising:
a transmit circuit that outputs test pulses to a probe including a transducer to generate an image of a test object, wherein a composite signal including the test pulses and a reflected signal is output by the transducer;
a receive circuit that receives the composite signal including the test pulses and the reflected signal and that includes a filter circuit that filters the test pulses from the composite signal and passes the reflected signal,
wherein an impedance of the filter circuit is equal to substantially zero when the reflected signal is within a predetermined frequency range, and
wherein the filter circuit includes a diode bridge; and
a bias resistor connected between a bias voltage and the diode bridge,
wherein a magnitude of the bias voltage is less than a magnitude of the test pulses, and
wherein a maximum value of the reflected signal is less than the magnitude of the bias voltage.

2. The transceiver of claim 1 wherein diodes of the diode bridge have forward transit times that are greater than one divided by a product of $2\pi$ and a minimum value of the predetermined frequency range.

3. The transceiver of claim 1 wherein the diode bridge is a full-bridge.

4. The transceiver of claim 1 further comprising
a clipper circuit that communicates with an output of the filter circuit and that limits a magnitude of the output of the filter circuit to less than the magnitude of the bias voltage; and
an amplifier that amplifies the output of the filter circuit.

5. The transceiver of claim 4 wherein the amplifier includes a low noise amplifier (LNA).

6. The transceiver of claim 4 wherein the clipper circuit includes a first diode connected between the output of the filter circuit and a reference potential and a second diode connected anti-parallel to the first diode between the output of the filter circuit and the reference potential.

7. The transceiver of claim 1 wherein zero inductors are connected between the bias voltage and the bias resistor.

8. The transceiver of claim 1 wherein the filter circuit includes a bridge of diodes having forward transit times that are greater than one divided by a product of $2\pi$ and a minimum value of the predetermined frequency range by at least a predetermined amount.

9. The transceiver of claim 1 further comprising:
an amplifier that communicates with an output of the filter circuit, that amplifies a voltage at the output, and that outputs an amplified voltage; and
a processing module that generates a signal for displaying the image of the test object based on the amplified voltage.

10. The transceiver of claim 1 wherein the impedance is greater than substantially zero when the reflected signal is less than a minimum value of the predetermined frequency range.

11. A transceiver for an ultrasonic imaging device, comprising:
a transmit circuit that outputs test pulses to a probe including a transducer to generate an image of a test object, wherein a composite signal including the test pulses and a reflected signal is output by the transducer;
a diode bridge that receives the composite signal including the test pulses and the reflected signal and that filters the test pulses from the composite signal and passes the reflected signal,
wherein each of the diodes of the diode bridge has a forward transit time that is greater than one divided by a product of $2\pi$ and a minimum value of a predetermined frequency range of the reflected signal; and
a bias resistor connected between a bias voltage and the diode bridge,
wherein a magnitude of the bias voltage is less than a magnitude of the test pulses, and
wherein a maximum value of the reflected signal is less than the magnitude of the bias voltage.

12. The transceiver of claim 11 wherein the forward transit time is greater than one divided by the product of $2\pi$ and the minimum value of the predetermined frequency range by a predetermined amount.

13. The transceiver of claim 11 wherein the diode bridge is a full-bridge.

14. The transceiver of claim 11 further comprising:
a clipper circuit that communicates with an output of the diode bridge and that limits a magnitude of the output of the diode bridge to less than the magnitude of the bias voltage;
an amplifier that communicates with an output of the diode bridge, that amplifies a voltage at the output, and that outputs an amplified voltage; and a processing module that generates a signal for displaying the image of the test object based on the amplified voltage.

15. The transceiver of claim 14 wherein the amplifier includes a low noise amplifier (LNA).

16. The transceiver of claim 11 wherein zero inductors are connected between the bias voltage and the bias resistor.

17. A transceiver for an ultrasonic imaging device, comprising:
- a transmit circuit that outputs test pulses of a first magnitude to a probe including a transducer to generate an image of a test object,
- wherein a composite signal including the test pulses and a reflected signal is output by the transducer, and
- wherein a maximum magnitude of the reflected signal is less than the first magnitude;
- a diode bridge that receives the composite signal including the test pulses and the reflected signal and that includes diodes having forward transit times that are each greater than one divided by a product of $2\pi$ and a minimum value of a predetermined frequency range of the reflected signal; and
- a bias resistor connected between a bias voltage and the diode bridge,
- wherein a second magnitude of the bias voltage is greater than the maximum magnitude and less than the first magnitude, and
- wherein the diode bridge filters voltages of the composite signal that are greater than the bias voltage and passes voltages of the composite signal that are less than the bias voltage.

18. The transceiver of claim 17 wherein the diode bridge is a full-bridge.

* * * * *

UNITED STATES PATENT AND TRADEMARK OFFICE
CERTIFICATE OF CORRECTION

| | | |
|---|---|---|
| PATENT NO. | : 8,804,457 B2 | Page 1 of 1 |
| APPLICATION NO. | : 13/077252 | |
| DATED | : August 12, 2014 | |
| INVENTOR(S) | : Luigi Franchini et al. | |

It is certified that error appears in the above-identified patent and that said Letters Patent is hereby corrected as shown below:

In the Specification:

Column 9, Line 34        Delete "Can" and insert --can--

In the Claims:

Column 10, Line 1, Claim 4      After "comprising", insert --:--

Signed and Sealed this
Eighteenth Day of November, 2014

Michelle K. Lee
*Deputy Director of the United States Patent and Trademark Office*